US011850122B2

(12) United States Patent
Luckemeyer et al.

(10) Patent No.: US 11,850,122 B2
(45) Date of Patent: Dec. 26, 2023

(54) WOUND DRESSING WITH HUMIDITY COLORIMETER SENSOR

(71) Applicant: KCI LICENSING, INC., San Antonio, TX (US)

(72) Inventors: James A. Luckemeyer, San Antonio, TX (US); Christopher B. Locke, Bournemouth (GB)

(73) Assignee: 3M Innovative Properties Company, Saint Paul, MN (US)

( * ) Notice: Subject to any disclaimer, the term of this patent is extended or adjusted under 35 U.S.C. 154(b) by 589 days.

(21) Appl. No.: 16/760,850

(22) PCT Filed: Oct. 30, 2018

(86) PCT No.: PCT/US2018/058119
§ 371 (c)(1),
(2) Date: Apr. 30, 2020

(87) PCT Pub. No.: WO2019/089522
PCT Pub. Date: May 9, 2019

(65) Prior Publication Data
US 2020/0289328 A1    Sep. 17, 2020

Related U.S. Application Data

(60) Provisional application No. 62/580,853, filed on Nov. 2, 2017.

(51) Int. Cl.
*A61F 13/00* (2006.01)
*A61B 5/00* (2006.01)
*A61F 13/02* (2006.01)

(52) U.S. Cl.
CPC ........ *A61F 13/00055* (2013.01); *A61B 5/445* (2013.01); *A61F 13/0209* (2013.01);
(Continued)

(58) Field of Classification Search
CPC ............ A61F 13/00055; A61F 13/0209; A61F 13/0243; A61F 13/0223;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU    550575 B2    3/1986
AU    745271 B2    3/2002
(Continued)

OTHER PUBLICATIONS

International Search Report and Written Opinion in International Application No. PCT/US2018/058119, dated Jan. 28, 2019.
(Continued)

*Primary Examiner* — Tarla R Patel (57) ABSTRACT

A wound dressing includes a superabsorbent pad, a drape layer, a humidity chamber, a wick, and a humidity colorimeter sensor. The superabsorbent pad is configured to absorb wound fluid and has a first side and a second, wound-facing side. The drape layer is coupled to the first side of the superabsorbent pad and has a first side and a second, wound-facing side. The drape layer is substantially impermeable to liquid and substantially permeable to vapor. The humidity chamber is coupled to the first side of the drape layer opposite the superabsorbent pad. The wick extends through the drape layer and is configured to wick moisture between the superabsorbent pad and the humidity chamber. The humidity colorimeter sensor is located within the humidity chamber and configured to change color responsive to a humidity level within the humidity chamber.

19 Claims, 4 Drawing Sheets

(52) U.S. Cl.
CPC .... *A61F 13/0243* (2013.01); *A61B 2562/029* (2013.01); *A61F 13/0223* (2013.01); *A61F 2013/00748* (2013.01); *A61F 2013/00876* (2013.01); *A61F 2013/00944* (2013.01)

(58) Field of Classification Search
CPC .. A61F 2013/00748; A61F 2013/00876; A61F 2013/00944; A61F 2013/00855; A61F 13/00059; A61F 13/00; A61F 5/40; A61F 5/008; A61F 35/006; A61B 5/445; A61B 2562/029; A61B 2560/0214; A61B 5/0013; A61B 5/6833; A61L 15/44; A61L 15/00; A61N 5/1029; A61M 16/047
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2015/0018792 A1 | 1/2015 | Marsiquet et al. | |
| 2016/0331593 A1* | 11/2016 | Revol-Cavalier | A61F 13/42 |

FOREIGN PATENT DOCUMENTS

| | | | |
|---|---|---|---|
| AU | 755496 B2 | 12/2002 | |
| CA | 2005436 A1 | 6/1990 | |
| CA | 3074639 A1 * | 3/2019 | ........... A61B 5/0013 |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 3 034 054 A1 | 6/2016 | |
| EP | 3034054 A1 * | 6/2016 | ............... A61B 5/00 |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |

(56) References Cited

FOREIGN PATENT DOCUMENTS

| | | |
|---|---|---|
| WO | 99/13793 A1 | 3/1999 |
| WO | WO-99/12581 A2 | 3/1999 |
| WO | WO-2013/013197 A1 | 1/2013 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All—Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

WOUND DRESSING WITH HUMIDITY COLORIMETER SENSOR

CROSS-REFERENCE TO RELATED APPLICATIONS

This application claims the benefit of priority under 35 U.S.C. § 371 to international patent application number PCT/US2018/058119, having a filing date of Oct. 30, 2018, which claims the benefit of priority to U.S. Provisional Application No. 62/580,853, filed on Nov. 2, 2017, which are both incorporated herein by reference in their entirety.

BACKGROUND

The present disclosure relates generally to a wound dressing and more particularly to a wound dressing configured to monitor moisture level at a wound site.

Maintaining a suitable level of moisture at a wound site can promote wound healing. However, it can be difficult to monitor the moisture level at the wound site, except by removing the wound dressing and directly observing the wound. Selecting an appropriate level of absorbency for the wound dressing can be important for several reasons. A wound dressing that is too absorbent can over-dry the wound site, whereas a wound dressing that is not absorbent enough can saturate with wound exudate and result in a wet wound site. It would be desirable to accurately monitor and control the level of moisture of a wound site in order to promote effective wound healing.

SUMMARY

One implementation of the present disclosure is a wound dressing including a superabsorbent pad, a drape layer, a humidity chamber, a wick, and a humidity colorimeter sensor. The superabsorbent pad is configured to absorb wound fluid and has a first side and a second, wound-facing side. The drape layer is coupled to the first side of the superabsorbent pad and has a first side and a second, wound-facing side. The drape layer is substantially impermeable to liquid and substantially permeable to vapor. The humidity chamber is coupled to the first side of the drape layer opposite the superabsorbent pad. The wick extends through the drape layer and is configured to wick moisture between the superabsorbent pad and the humidity chamber. The humidity colorimeter sensor is located within the humidity chamber and configured to change color responsive to a humidity level within the humidity chamber.

In some embodiments, the humidity colorimeter sensor includes a graphene oxide sensor. In some embodiments, the humidity colorimeter sensor includes a non-powered humidity sensor.

In some embodiments, the humidity chamber is substantially impermeable to liquid and substantially permeable to vapor. In some embodiments, the humidity chamber is substantially impermeable to both liquid and vapor.

In some embodiments, the humidity chamber includes an outer layer having a perimeter adhered to the first side of the drape layer, thereby sealing the humidity colorimeter sensor between the outer layer and the drape layer. In some embodiments, the drape layer is configured to transfer moisture vapor through the drape layer at a first moisture vapor transmission rate and the outer layer of the humidity chamber is configured to transfer moisture vapor through the outer layer at a second moisture vapor transmission rate less than the first moisture vapor transmission rate.

In some embodiments, the humidity chamber includes an outer layer and an inner layer positioned between the outer layer and the first side of the drape layer. The inner layer may have a perimeter adhered to the outer layer, thereby sealing the humidity colorimeter sensor between the outer layer and the inner layer. In some embodiments, the wick extends through both the drape layer and the inner layer of the humidity chamber.

In some embodiments, the wick includes a first end portion located between the superabsorbent pad and the drape layer, a second end portion located within the humidity chamber, and a middle portion extending through the drape layer and connecting the first end portion and the second end portion. In some embodiments, the first end portion and the second end portion are substantially parallel to the superabsorbent pad and the drape layer. In some embodiments, the middle portion is substantially perpendicular to the superabsorbent pad and the drape layer.

In some embodiments, the drape layer includes a polyurethane film. In some embodiments, the drape layer is configured to wick moisture from the superabsorbent pad and distribute the moisture across the first side of the drape layer.

In some embodiments, the wound dressing includes an adhesive coating coupled to the second, wound-facing side of the drape layer. In some embodiments, the drape layer extends beyond a perimeter of the superabsorbent pad to provide an adhesive-coated margin configured to adhere the wound dressing to a surface.

Another implementation of the present disclosure is a wound dressing including a superabsorbent pad, a humidity chamber, and a humidity colorimeter sensor. The superabsorbent pad is configured to absorb wound fluid and has a first side and a second, wound-facing side. The humidity chamber is located on the first side of the superabsorbent pad. The humidity colorimeter sensor is located within the humidity chamber and configured to change color responsive to a humidity level within the humidity chamber.

In some embodiments, the humidity colorimeter sensor includes a graphene oxide sensor. In some embodiments, the humidity colorimeter sensor includes a non-powered humidity sensor.

In some embodiments, the humidity chamber is substantially impermeable to liquid and substantially permeable to vapor. In some embodiments, the humidity chamber is substantially impermeable to both liquid and vapor.

In some embodiments, the wound dressing includes a wick configured to wick moisture between the superabsorbent pad and the humidity chamber.

In some embodiments, the wound dressing includes a drape layer positioned between the superabsorbent pad and the humidity chamber. The drape layer may be substantially impermeable to liquid and substantially permeable to vapor. In some embodiments, the wound dressing includes a wick extending through the drape layer and configured to wick moisture between the superabsorbent pad and the humidity chamber.

In some embodiments, the wick includes a first end positioned between the superabsorbent pad and the drape layer, a second end positioned within the humidity chamber, and a middle portion extending through the drape layer and connecting the first end and the second end. In some embodiments, the first end portion and the second end portion are substantially parallel to the superabsorbent pad and the drape layer. In some embodiments, the middle portion is substantially perpendicular to the superabsorbent pad and the drape layer.

In some embodiments, the humidity chamber includes an outer layer having a perimeter adhered to the drape layer, thereby sealing the humidity colorimeter sensor between the outer layer and the drape layer. In some embodiments, the drape layer is configured to transfer moisture vapor through the drape layer at a first moisture vapor transmission rate and the outer layer of the humidity chamber is configured to transfer moisture vapor through the outer layer at a second moisture vapor transmission rate less than the first moisture vapor transmission rate.

In some embodiments, the humidity chamber includes an outer layer and an inner layer positioned between the outer layer and the drape layer. The inner layer may have a perimeter adhered to the outer layer, thereby sealing the humidity colorimeter sensor between the outer layer and the inner layer. In some embodiments, the wick extends through both the drape layer and the inner layer of the humidity chamber.

In some embodiments, the drape layer includes a polyurethane film. In some embodiments, the drape layer is configured to wick moisture from the superabsorbent pad and distribute the moisture across a first side of the drape layer opposite the superabsorbent pad.

In some embodiments, the wound dressing includes an adhesive coating coupled to a second, wound-facing side of the drape layer. In some embodiments, the drape layer extends beyond a perimeter of the superabsorbent pad to provide an adhesive-coated margin configured to adhere the wound dressing to a surface.

Another implementation of the present disclosure is a system for monitoring humidity of a wound site. The system includes a wound dressing including a humidity colorimeter sensor configured to measure the humidity of the wound site and to emit or reflect light at a wavelength representative of the humidity of the wound site. The wavelength of the light emitted or reflected by the humidity colorimeter sensor is within a spectrum readable by an electronic device to allow the electronic device to determine the humidity of the wound site based on the wavelength of the light.

In some embodiments, the humidity colorimeter sensor includes a graphene oxide sensor. In some embodiments, the humidity colorimeter sensor includes a non-powered humidity sensor.

In some embodiments, the electronic device includes a photo sensor configured to detect the wavelength of the light emitted or reflected by the humidity colorimeter sensor and a processing circuit configured to determine the humidity of the wound site based on the wavelength of the light detected by the photo sensor.

In some embodiments, the electronic device is a smartphone having a camera that includes the photo sensor. The processing circuit includes an application installed on the smartphone. The application may be configured to determine the humidity of the wound site based on the wavelength of the light detected by photo sensor.

In some embodiments, the wound dressing includes a superabsorbent pad configured to absorb wound fluid and having a first side and a second, wound-facing side. The wound dressing may include a humidity chamber located on the first side of the superabsorbent pad. The humidity colorimeter sensor may be located within the humidity chamber and configured to change color responsive to a humidity change within the humidity chamber.

In some embodiments, the humidity chamber is substantially impermeable to liquid and substantially permeable to vapor. In some embodiments, the humidity chamber is substantially impermeable to both liquid and vapor.

In some embodiments, the wound dressing includes a drape layer positioned between the superabsorbent pad and the humidity chamber. The drape layer may be substantially impermeable to liquid and substantially permeable to vapor.

In some embodiments, the wound dressing includes a wick configured to wick moisture between the superabsorbent pad and the humidity chamber. In some embodiments, the wick extends through the drape layer.

In some embodiments, the wick includes a first end positioned between the superabsorbent pad and the drape layer, a second end positioned within the humidity chamber, and a middle portion extending through the drape layer and connecting the first end and the second end. In some embodiments, the first end portion and the second end portion are substantially parallel to the superabsorbent pad and the drape layer. In some embodiments, the middle portion is substantially perpendicular to the superabsorbent pad and the drape layer.

In some embodiments, the humidity chamber includes an outer layer having a perimeter adhered to the drape layer, thereby sealing the humidity colorimeter sensor between the outer layer and the drape layer.

In some embodiments, the drape layer is configured to transfer moisture vapor through the drape layer at a first moisture vapor transmission rate and the outer layer of the humidity chamber is configured to transfer moisture vapor through the outer layer at a second moisture vapor transmission rate less than the first moisture vapor transmission rate.

In some embodiments, the humidity chamber includes an outer layer and an inner layer positioned between the outer layer and the drape layer. The inner layer may have a perimeter adhered to the outer layer, thereby sealing the humidity colorimeter sensor between the outer layer and the inner layer. In some embodiments, the wick extends through both the drape layer and the inner layer of the humidity chamber.

In some embodiments, the drape layer includes a polyurethane film. In some embodiments, the drape layer is configured to wick moisture from the superabsorbent pad and distribute the moisture across a first side of the drape layer opposite the superabsorbent pad.

In some embodiments, the wound dressing includes an adhesive coating coupled to a second, wound-facing side of the drape layer. In some embodiments, the drape layer extends beyond a perimeter of the superabsorbent pad to provide an adhesive-coated margin configured to adhere the wound dressing to a surface.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a wound dressing with a humidity colorimeter sensor is shown, according to various exemplary embodiments. The wound dressing may include a superabsorbent pad, a drape layer, a humidity chamber, a wick, and a humidity colorimeter sensor. The superabsorbent pad can be configured to absorb wound fluid and may include a first side and a second, wound-facing side. The drape layer may be coupled to the first side of the superabsorbent pad. The drape layer may also include a first side and a second, wound-facing side. In some embodiments, the drape layer is substantially impermeable to liquid and substantially permeable to vapor. The humidity chamber may be coupled to the first side of the drape layer opposite the superabsorbent pad.

The wick may include a first end portion located between the drape layer and the superabsorbent pad and a second end portion located within the humidity chamber. The wick may extend through the drape layer and may be configured to wick moisture between the superabsorbent pad and the humidity chamber. The humidity colorimeter sensor may be located within the humidity chamber and configured to change color responsive to a humidity level within the humidity chamber. In some embodiments, an electronic device can be used to measure the color of the humidity colorimeter sensor and determine a humidity level based on the measured color. These and other features of the wound dressing and electronic device are described in greater detail below.

Wound Dressing

Figure 1:
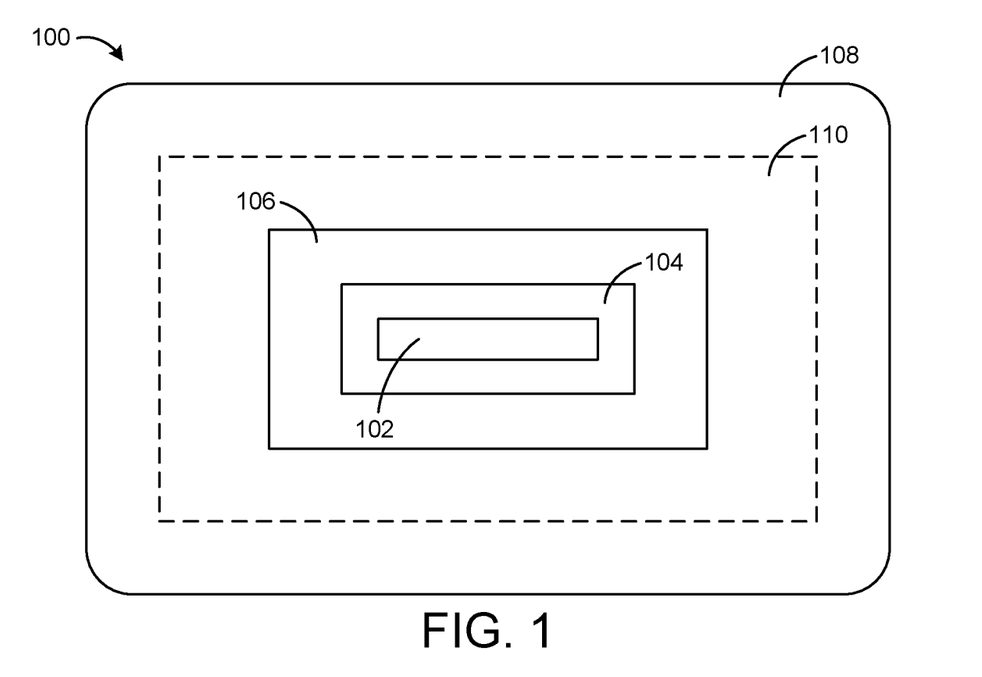
FIG. 1 is a top view of a wound dressing as would be visible when the wound dressing is adhered to a surface (e.g., a patient's skin), according to an exemplary embodiment.
Figure 2:
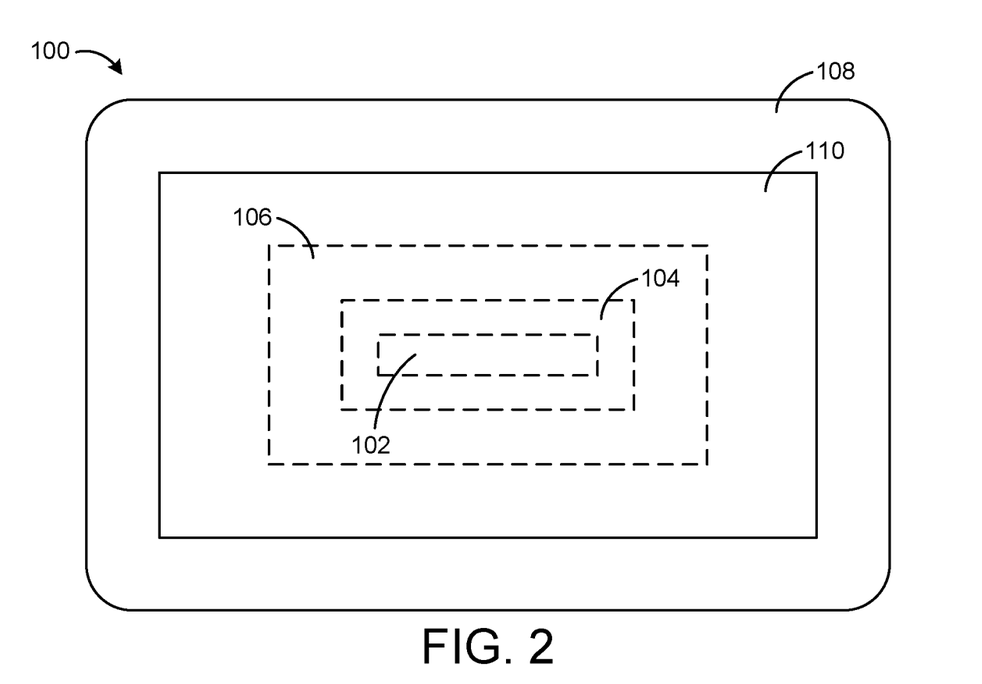
FIG. 2 is a bottom view of the wound dressing of FIG. 1 showing the wound-contacting surface of the wound dressing, according to an exemplary embodiment.
Figure 3:
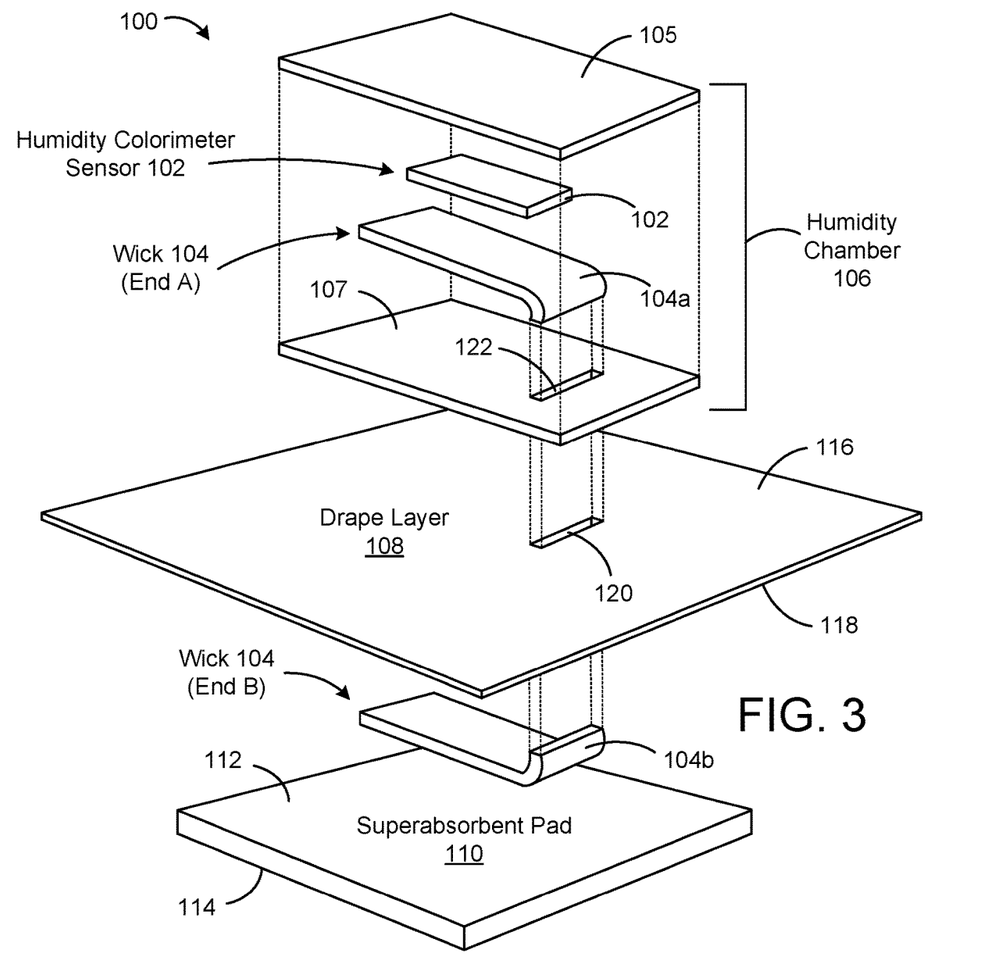
FIG. 3 is an exploded view illustrating several layers of the wound dressing of FIG. 1, according to an exemplary embodiment.
Figure 4:
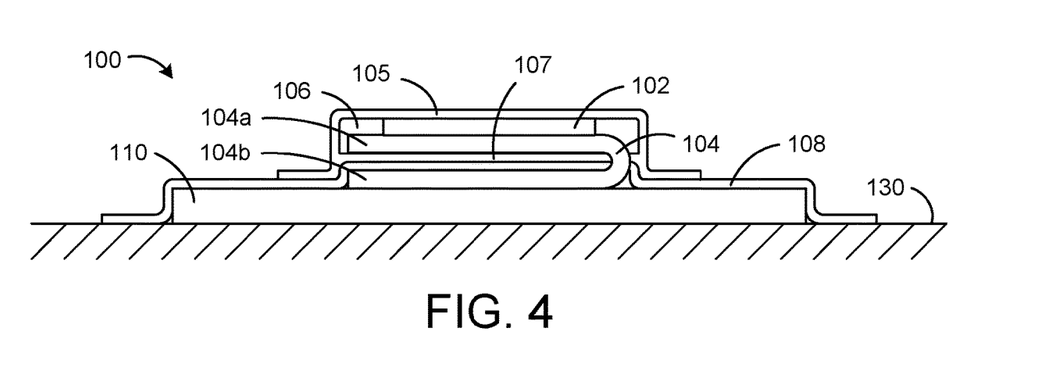
FIG. 4 is a cross-sectional view of the wound dressing of FIG. 1 adhered to a surface, according to an exemplary embodiment.

Referring now to FIGS. 1-4, a wound dressing 100 is shown, according to an exemplary embodiment. In brief overview, FIG. 1 is a top view of wound dressing 100 as would be visible when wound dressing 100 is adhered to a surface (e.g., a patient's skin). FIG. 2 is a bottom view of wound dressing 100 showing the wound-contacting surface of wound dressing 100. The broken lines in FIGS. 1-2 outline the layers of wound dressing 100 that are not visible in each view. FIG. 3 is an exploded view illustrating several layers 102-110 of wound dressing 100. FIG. 4 is a cross-sectional view of wound dressing 100 adhered to a surface 130.

In various embodiments, wound dressing 100 can be formed as a substantially flat sheet for topical application to wounds or contoured for application to body surfaces having high curvature. The size of wound dressing 100 can vary depending on the size of the wound to be dressed. For example, it is contemplated that the size of wound dressing 100 can range from 1 $cm^2$ to 200 $cm^2$, and more preferably from 4 $cm^2$ to 100 $cm^2$. However, other shapes and sizes of wound dressing 100 are also possible depending on the intended use. Wound dressing 100 is shown to include superabsorbent pad 110, a drape layer 108, a humidity chamber 106, a wick 104, and a humidity colorimeter sensor 102. Each of these components of wound dressing 100 is described in detail below.

Superabsorbent Pad

Superabsorbent pad 110 can be configured to absorb wound fluid and is shown to include a first side 112 and a second, wound-facing side 114. When wound dressing 100 is applied to a wound, first side 112 faces away from the wound, whereas second side 114 faces toward the wound. In some embodiments, first side 112 of superabsorbent pad 110 contacts the wound-facing side 118 of drape layer 108. Similarly, second side 114 of superabsorbent pad 110 may contact a surface 130 to which wound dressing 100 is applied (e.g., a patient's skin, a wound, etc.). Superabsorbent pad 110 can be configured to wick moisture from the wound and distribute the moisture across first side 112.

In some embodiments, superabsorbent pad 110 includes a superabsorbent layer along first side 112 and a hydrophilic foam layer along second side 114. The superabsorbent layer can be laminated to the hydrophilic foam layer using a fusible fiber positioned between the superabsorbent layer and the hydrophilic foam layer. In some embodiments, the superabsorbent layer includes a hydrogel or hydrogel composition. Several examples of hydrogels and hydrogel compositions which can be used to form superabsorbent pad 110 are described in detail in U.S. Pat. No. 8,097,272 issued Jan. 17, 2012, U.S. Pat. No. 8,664,464 issued Mar. 4, 2014, and U.S. Pat. No. 8,058,499 issued Nov. 15, 2011. The entire disclosure of each of these patents is incorporated by reference herein.

The expressions "hydrogel" and "hydrogel compositions" used herein are not to be considered as limited to gels which contain water, but extend generally to all hydrophilic gels and gel compositions, including those containing organic non-polymeric components in the absence of water. For example, the superabsorbent layer may be formed from a polyurethane that entraps water to form a gel. In some embodiments, the superabsorbent layer is substantially continuous and/or substantially non-porous or non-foamed. The superabsorbent layer may include a flexible plasticized hydrophilic polymer matrix having a substantially continuous internal structure. The density of the superabsorbent layer may be greater than 0.5 $g/cm^3$, more preferably greater than 0.8 $g/cm^3$, and most preferably from 0.9 to 1.1 $g/cm^3$. In some embodiments, the thickness of the superabsorbent layer is from 1 mm to 10 mm, more preferably from 2 mm to 5 mm.

In some embodiments, the superabsorbent layer is cross-linked and preferably it is substantially insoluble in water at ambient temperature. However, the structure of the superabsorbent layer absorbs and entraps liquid to provide a highly hydrated gel structure in contrast to the porous foam structure of the hydrophilic foam layer. Preferably, the gel can absorb 1 to 10 g/g of physiological saline at 20°, more preferably 2 to 5 g/g.

In some embodiments, the dry weight of the superabsorbent layer is from 1000 to 5000 $g/m^2$, more preferably from 2000 to 4000 $g/m^2$. In some embodiments, the superabsorbent layer includes from 1% to 30% of water, more preferably from 10% to 20% by weight of water before use. In some embodiments, the superabsorbent layer contains from 1% to 40%, more preferably from 5 to 15%, by weight of one or more humectants, preferably selected from the group consisting of glycerol, propylene glycol, sorbitol, mannitol, polydextrose, sodium pyrrolidine carboxylic acid (NaPCA), hyaluronic acid, aloe, jojoba, lactic acid, urea, gelatin, lecithin and mixtures thereof. The entrapped water and optional humectants give the hydrogel a soft, moist wound-friendly surface for contacting the wound.

The hydrophilic foam layer can be positioned between the superabsorbent layer and the wound. In some embodiments, the hydrophilic foam layer is laminated to the superabsorbent layer using a fusible fiber positioned between the superabsorbent layer and the hydrophilic foam layer. The superabsorbent layer can be bonded to the hydrophilic foam layer, for example by an adhesive or by radiation cross-linking. In some embodiments, the superabsorbent layer is bonded to the hydrophilic foam layer by urethane or urea linkages. This can be achieved by applying the hydrophilic foam layer to the superabsorbent layer (substantially without mixing) before polyurethane curing is complete.

The hydrophilic foam layer may include a polyurethane foam coupled to the superabsorbent layer. In some embodiments, the hydrophilic foam layer includes a flexible plasticized hydrophilic polymer matrix having an internal cellular structure. Several examples of hydrophilic foams which can be used to form the hydrophilic foam layer are described in detail in U.S. Pat. No. 8,097,272 issued Jan. 17, 2012, U.S. Pat. No. 8,664,464 issued Mar. 4, 2014, and U.S. Pat. No. 8,058,499 issued Nov. 15, 2011. The entire disclosure of each of these patents is incorporated by reference herein.

Advantageously, the hydrophilic foam layer may provide enhanced absorbency for liquid exudate. This is because the initial substantially anhydrous condition and porous structure of the hydrophilic foam layer enables it to absorb a larger amount of water by both chemical and physical absorption that is the case for the corresponding hydrogel material. Furthermore, the porous structure of the foam provides for rapid uptake of liquid exudate, in contrast to pure hydrogel dressings.

In some embodiments, the hydrophilic foam layer has a thickness of from 1 to 20 mm, more preferably from 1.5 to 5 mm. In some embodiments, the hydrophilic foam layer has a density of from 0.28 $g/cm^3$ to 0.5 $g/cm^3$, and more preferably from 0.32 $g/cm^3$ to 0.48 $g/cm^3$. Preferably, the hydrophilic foam layer has an elongation to break of at least 150%, more preferably from 500% to 1000%. The foam that forms the hydrophilic foam layer may be hydrophilic and can absorb aqueous fluids such as wound exudate with swelling. The hydrophilic foam layer may be highly cross-linked and substantially insoluble in water.

In some embodiments, the hydrophilic foam layer has an absorbency of at least 3 grams of saline per gram of foam, and preferably a swellability in water of at least 200%. In some embodiments, the hydrophilic foam layer is constructed using the foam as described in European Patent No. 0541391 issued Jun. 10, 1998, the entire disclosure of which is incorporated by reference herein. In some embodiments, the hydrophilic foam layer includes less than 10% water prior to use as an absorbent, more preferably less than 5% water, and even more preferably it contains less than 2% of water before use.

Drape Layer

Drape layer 108 is shown to include a first side 116 and a second, wound-facing side 118 opposite first side 116. When wound dressing 100 is applied to a wound, first side 116 faces away from the wound, whereas second side 118 faces toward the wound. Drape layer 108 supports superabsorbent pad 110 and provides a barrier to passage of microorganisms through wound dressing 100. In some embodiments, drape layer 108 is a thin layer of polyurethane film. One example of a suitable material for drape layer 108 is the polyurethane film known as ESTANE 5714F. Other suitable polymers for forming drape layer 108 include poly alkoxyalkyl acrylates and methacrylates, such as those described in Great Britain Patent Application No. 1280631A filed Nov. 22, 2002, the entire disclosure of which is incorporated by reference herein. In some embodiments, drape layer 108 includes a continuous layer of a high-density blocked polyurethane foam that is predominantly closed-cell. Drape layer 108 may have a thickness in the range of 10 μm to 100 μm, preferably in the range of 50 μm to 70 μm. In some embodiments, drape layer 108 has a thickness of approximately 60 μm.

Drape layer 108 may be substantially impermeable to liquid and substantially permeable to moisture vapor. In other words, drape layer 108 may be permeable to water vapor, but not permeable to liquid water or wound exudate. This increases the total fluid handling capacity (TFHC) of wound dressing 100 while promoting a moist wound environment. In some embodiments, drape layer 108 is also impermeable to bacteria and other microorganisms. Drape layer 108 may have a moisture vapor transmission rate (MVTR) of approximately 300 to 5000 grams per meter$^2$ ($g/m^2$) per twenty-four hours, preferably 500 to 2000 $g/m^2$ per twenty-four hours at 37.5° C. at 100% to 10% relative humidity difference. In some embodiments, drape layer 108 is configured to wick moisture from superabsorbent pad 110 and distribute the moisture across first side 116.

Side 118 of drape layer 108 may be coated with an acrylic or other adhesive. The adhesive applied to side 118 ensures that wound dressing 100 adheres to surface 130 and that wound dressing 100 remains in place throughout the wear time. In some embodiments, the perimeter of drape layer 108 extends beyond (e.g., circumscribes) the perimeter of superabsorbent pad 110 to provide an adhesive-coated margin for adhering wound dressing 100 to the skin of a patient adjacent to the wound being treated, shown in FIG. 4 as surface 130. The adhesive-coated margin may extend around all sides of superabsorbent pad 110 such that wound dressing 100 is a so-called island dressing. In other embodiments, the adhesive-coated margin can be eliminated and wound dressing 100 can be adhered to surface 130 using other techniques.

In some embodiments, side 118 of drape layer 108 contacts contact side 112 of superabsorbent pad 110. Side 118 of drape layer 108 may adhere to side 112 of superabsorbent pad 110 along the portion of drape layer 108 that overlaps with superabsorbent pad 110. In this way, drape layer 108 and superabsorbent pad 110 may form a closed pocket, sealing end portion 104b of wick 104 between drape layer 108 and superabsorbent pad 110. In some embodiments, drape layer 108 includes an aperture 120 (e.g., a hole, slot, opening, etc.) through which wick 104 passes. Wick 104 may extend through aperture 120 such that end portion 104a of wick 104 is located on one side of drape layer 108 (e.g., within humidity chamber 106) whereas end portion 104b of wick 104 is located on the opposite side of drape layer 108 (e.g., between drape layer 108 and superabsorbent pad 110).

In some embodiments, the adhesive applied to side 118 of drape layer 108 is moisture vapor transmitting and/or patterned to allow passage of water vapor therethrough. The adhesive may include a continuous moisture vapor transmitting, pressure-sensitive adhesive layer of the type, conventionally used for island-type wound dressings (e.g., a polyurethane-based pressure sensitive adhesive). One example of an adhesive which can be used is a pressure sensitive adhesive based on acrylate ester copolymers, polyvinyl ethyl ether and polyurethane, as described in Great Britain Patent Application No. 1280631A. The basis weight of the adhesive may be 20 to 250 g/m$^2$, and more preferably 50 to 150 g/m$^2$.

Humidity Chamber

Humidity chamber 106 may be coupled to first side 116 of drape layer 108, opposite superabsorbent pad 110, and may include an outer layer 105 and an inner layer 107. The perimeters of outer layer 105 and inner layer 107 can be coupled to each other to define humidity chamber 106 between outer layer 105 and inner layer 107. In some embodiments, layers 105 and 107 of humidity chamber 106 are substantially impermeable to liquid and substantially permeable to vapor. In other embodiments, layers 105 and 107 of humidity chamber 106 are substantially impermeable to both liquid and vapor.

As shown in FIGS. 3-4, inner layer 107 may be positioned between outer layer 105 and first side 116 of drape layer 108. The perimeter of inner layer 107 may be adhered to the perimeter of outer layer 105, thereby sealing humidity colorimeter sensor 102 between outer layer 105 and inner layer 107. Inner layer 107 can be adhered to first side 116 of drape layer to couple humidity chamber 106 to drape layer 108. In other embodiments, inner layer 107 can be omitted and the perimeter of outer layer 105 can be adhered directly to first side 116 of drape layer 108, thereby sealing humidity colorimeter sensor 102 between outer layer 105 and drape layer 108.

In some embodiments, outer layer 105, inner layer 107, and drape layer 108 are configured to provide various rates of moisture transfer through their respective layers. For example, drape layer 108 can be configured to transfer moisture through drape layer 108 at a first moisture vapor transmission rate (MVTR), whereas outer layer 105 may be configured to transfer moisture vapor through outer layer 105 at a second MVTR. In some embodiments, the second MVTR is less than the first MVTR (i.e., outer layer 105 is less permeable to moisture than drape layer 108). In other embodiments, the second MVTR is greater than the first MVTR (i.e., outer layer 105 is more permeable to moisture than drape layer 108). Similarly, inner layer 107 can be configured to transfer moisture vapor through inner layer 107 at a third MVTR. The third MVTR can be different from both the first MVTR and the second MVTR such that each of layers 105, 107, and 108 provides a different MVTR. In other embodiments, the third MVTR can be different from the first MVTR but the same as the second MVTR such that each of layers 105 and 107 provide the same MVTR.

Humidity chamber 106 can be configured to enclose a volume within which humidity colorimeter sensor 102 is located. The internal volume of humidity chamber 106 may be maintained at the same humidity level as superabsorbent pad 110 by the operation of wick 104. In some embodiments, humidity chamber 106 includes an aperture 122 (e.g., a hole, slot, opening, etc.) that extends through inner layer 107. Wick 104 may pass through aperture 122 such that end portion 104a of wick 104 is located on one side of inner layer 107 (e.g., within humidity chamber 106) whereas end portion 104b of wick 104 is located on the opposite side of inner layer 107 (e.g., outside humidity chamber 106, between drape layer 108 and superabsorbent pad 110). In some embodiments, wick 104 extends through both drape layer 108 (via aperture 120) and inner layer 107 (via aperture 122) such that both drape layer 108 and inner layer 107 are located between end portion 104a and end portion 104b of wick 104.

Wick

Wick 104 is shown to include a first end portion 104a located within humidity chamber 106 and a second end portion 104b located between superabsorbent pad 110 and drape layer 108. Although end portions 104a and 104b are shown as separate parts in FIG. 3 (for purposes of illustrating an exploded view), it should be understood that wick 104 may be a continuous structure that includes both end portions 104a and 104b and a middle portion that connects end portions 104a and 104b. In some embodiments, the middle portion of wick 104 includes a bend or fold (e.g., a 180 degree bend) such that wick 104 has a "C" shape (as shown in FIG. 4). End portions 104a and 104b can be arranged substantially parallel to each other and offset from each other by the thickness of layers 107 and 108 between end portions 104a and 104b. End portions 104a and 104b may be substantially parallel to both superabsorbent pad 110 and to drape layer 108, whereas the middle portion that connects end portions 104a and 104b may be substantially perpendicular to both superabsorbent pad 110 and drape layer 108

Wick 104 may extend through drape layer 108 and/or inner layer 107 and can be configured to wick (e.g., transfer) moisture between superabsorbent pad 110 and humidity chamber 106. In some embodiments, wick 104 equilibrates the humidity level within humidity chamber 106 with the humidity level of superabsorbent pad 110 and/or the humidity level of the wound site. Accordingly, the humidity level measured by colorimeter humidity sensor 102 within humidity chamber 106 may be the same as the humidity level of superabsorbent pad 110 and/or the wound site.

Wick 104 can be made of any material suitable for providing a wicking function to effectively transmit fluid between first end portion 104a and second end portion 104b. For example, wick 104 can be made of rayon or other suitable wicking fabric. Several examples of wicking materials that can be used in wick 104 are described in detail in U.S. patent application Ser. No. 13/009,238 filed Jan. 19, 2011, U.S. Pat. No. 6,936,037 filed Apr. 8, 2003, and U.S. Pat. No. 9,456,930 filed Mar. 17, 2014. The entire disclosure of each of these patents and patent applications is incorporated by reference herein. The wicking properties of wick 104 can be enhanced by using a hydrophilic material to form superabsorbent pad 110.

Wick 104 can be configured to transfer fluid bidirectionally between end portions 104a and 104b. For example, if the humidity level of superabsorbent pad 110 exceeds the humidity level within humidity chamber 106, wick 104 may transfer fluid from superabsorbent pad 110 to humidity chamber 106, thereby increasing the humidity level within humidity chamber 106. Conversely, if the humidity level of superabsorbent pad 110 is less than the humidity level of humidity chamber 106, wick 104 may transfer fluid from humidity chamber 106 to superabsorbent pad 110, thereby decreasing the humidity level within humidity chamber 106. Advantageously, the bidirectional wicking provided by wick 104 may allow the humidity level within humidity chamber 106 to increase or decrease in response to a change in humidity of superabsorbent pad 110 and/or at the wound site. In other words, wick 104 can cause the humidity level within humidity chamber 106 to equilibrate with the humidity level of superabsorbent pad 110 and/or the humidity level at the wound site.

The humidity equilibration caused by wick 104 may occur over a period of seconds (e.g., 30-60 seconds), minutes (e.g., 1-2 minutes, 2-5 minutes, 5-10 minutes, etc.), or any other time period. The shape of wick 104 (e.g., length, width, thickness, etc.) and material properties of wick 104 can be varied to adjust the equilibration time. For example, a thicker wick 104 may cause the humidity to equilibrate more quickly, whereas a thinner wick 104 may cause the humidity to equilibrate more slowly. It is contemplated that sensor 102 can respond to a change in humidity significantly faster than the change in humidity occurs such that the humidity level indicated by sensor 102 accurately represents the actual humidity level within humidity chamber 106.

Humidity Colorimeter Sensor

Humidity colorimeter sensor 102 may be located within humidity chamber 106 and can be configured to change color responsive to the humidity level within humidity chamber 106. The color of humidity colorimeter sensor 102 can be read (e.g., by a user or by an electronic device) as an indication of the humidity level within humidity chamber 106. For example, a user can compare the color of humidity colorimeter sensor 102 to a reference chart in order to interpret the humidity reading provided by sensor 102. The reference chart may include a range of colors and corresponding humidity values. The user can compare the color of humidity colorimeter sensor 102 and/or the corresponding humidity values to the ends of the range to determine whether the wound is too wet or too dry. An electronic device can measure the color of humidity colorimeter sensor 102 and automatically translate the color into a humidity value.

In some embodiments, outer layer 105 of humidity chamber 106 is transparent or substantially transparent to allow humidity colorimeter sensor 102 to be viewed or read through outer layer 105. Advantageously, humidity colorimeter sensor 102 may be a low-cost, disposable sensor, which is non-toxic and configured to provide a rapid response to a change in humidity within humidity chamber 106. In some embodiments, humidity colorimeter sensor 102 can respond to a change in humidity level within humidity chamber 106 within seconds (e.g., under 30 seconds, under 10 seconds, etc.) to provide a real-time indication of the humidity level within humidity chamber 106.

Although sensor 102 is described primarily as a humidity colorimeter sensor, it is contemplated that any type of humidity sensor can be used in wound dressing 100. For example, sensor 102 can be replaced with an electronic sensor configured to measure humidity and output a data signal or visual indication of the measured humidity value. In some embodiments, sensor 102 includes one or more LEDs (e.g., a red LED, a green LED, and a blue LED) that can be selectively powered or unpowered by sensor 102 to electronically create a color similar to the color displayed by a non-powered humidity colorimeter sensor. By increasing or decreasing the intensity of the light output by the colored LEDs, sensor 102 can blend the light output to create any color. Alternatively, sensor 102 can generate an electronic data signal that indicates the measured humidity and can transmit the data signal to an electronic device via a wired or wireless data connection. In some embodiments, sensor 102 is configured to detect the presence of both water vapor and specific other gases and can provide additional readings other than humidity.

Figure 5:
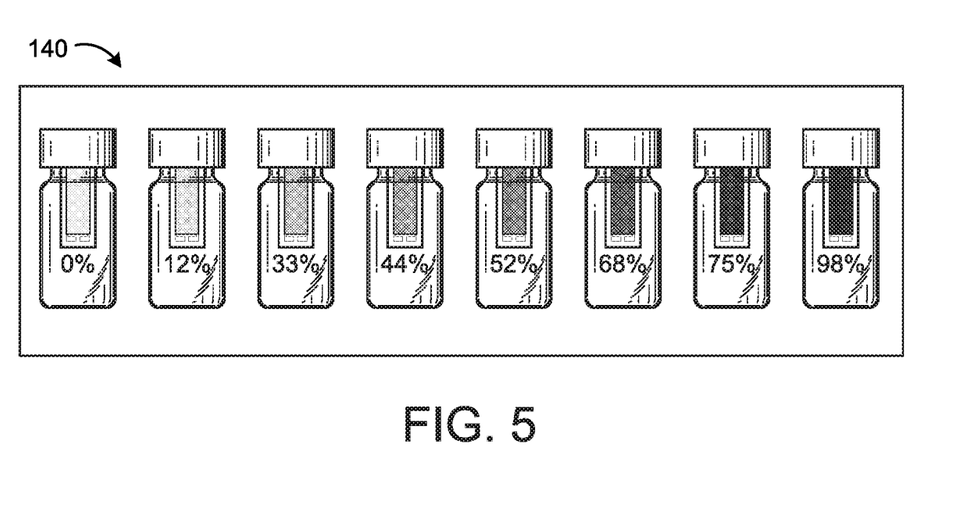
FIG. 5 is an array of graphene oxide (GO) based humidity sensors exposed to various humidity levels, according to an exemplary embodiment.

In some embodiments, humidity colorimeter sensor 102 includes a graphene oxide (GO) humidity sensor or other type of non-powered humidity sensor. GO-based humidity sensors can be configured to provide a direct indication of humidity by changing color based on the humidity level at the location of the GO-based sensor. For example, FIG. 5 shows an array 140 of GO-based humidity sensors exposed to various humidity levels ranging from 0% relative humidity to 98% relative humidity. The color of each GO-based humidity sensor is different and corresponds to the humidity level of the container within which the GO-based humidity sensor is located. In some embodiments, humidity colorimeter sensor 102 is a GO-based colorimetric sensor configured to respond to humidity levels by changing color that can be easily observed without requiring a power supply or other electronics.

In other embodiments, humidity colorimeter sensor 102 is a powered GO-based humidity sensor. One example of such a powered GO-based humidity sensor is described in detail in the non-patent publication "Ultrafast Graphene Oxide Humidity Sensors" *ACS Nano*, 2013, 7 (12), pp 11166-11173, published Nov. 9, 2013, the entire disclosure of which is incorporated by reference herein. In some embodiments, humidity colorimeter sensor 102 includes a two-dimensional graphene structure which is highly permeable to water molecules. Accordingly, the response time of humidity colorimeter sensor 102 (e.g., the time required to transition from displaying a color indicating 10% humidity to a color indicating 90% humidity and vice versa) may be less than 100 ms when a two-dimensional graphene structure is used.

Figure 6:
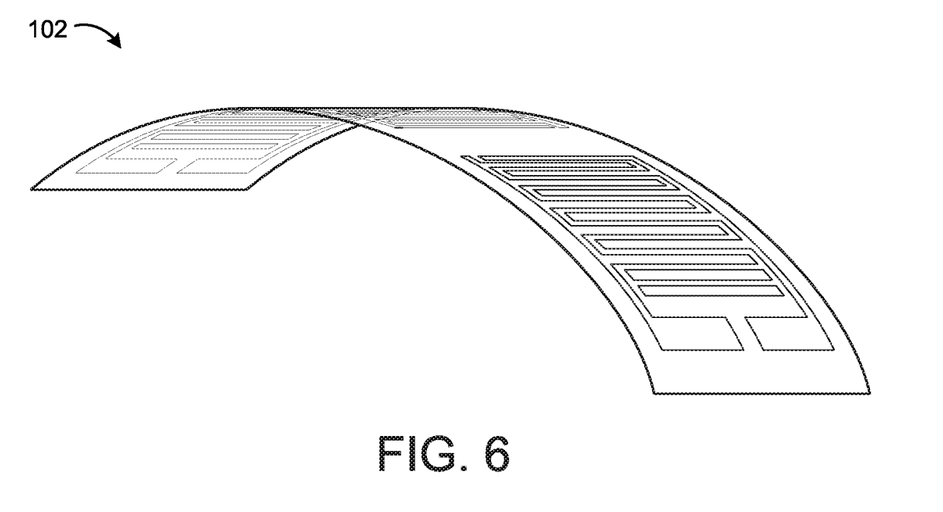
FIG. 6 is a drawing of a thin and flexible sensor which can be used in the wound dressing of FIG. 1, according to an exemplary embodiment.

In some embodiments, the sensing region of humidity colorimeter sensor 102 is thin (e.g., approximately 15 nm thick) and coupled to a physical substrate. The overall thickness of the physical substrate may be between 0.001 inches and 0.010 inches in various embodiments. However, it is contemplated that sensor 102 may be thicker or thinner in other embodiments. The thickness of sensor 102 can be decreased to increase flexibility or increased to make sensor 102 easier to handle and less likely to be damaged. Sensor 102 may be transparent, and/or flexible. An example of such a thin and flexible sensor 102 is shown in FIG. 6.

Although a power supply and/or other electronics are not required to use humidity colorimeter sensor 102, it is contemplated that an electronic device can be used to read or measure the color of humidity colorimeter sensor 102 to improve the accuracy of the humidity reading. Such an embodiment is described in greater detail below. Additionally, humidity colorimeter sensor 102 can be used in combination with a power supply (e.g., a battery) and wireless transmitter to transmit the humidity reading to an external device such as a smartphone or therapy unit. The battery and wireless transmitter can be located within wound dressing 100 or as part of an external therapy unit connected to wound dressing 100.

Humidity Monitoring System

Figure 7:
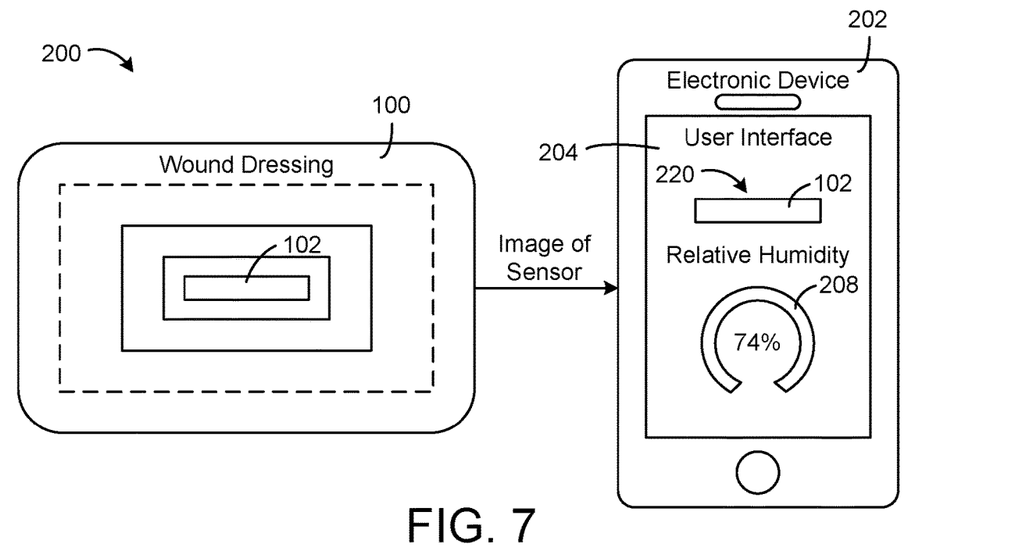
FIG. 7 is a drawing of a humidity monitoring system including the wound dressing of FIG. 1 and an electronic device, according to an exemplary embodiment.
Figure 8:
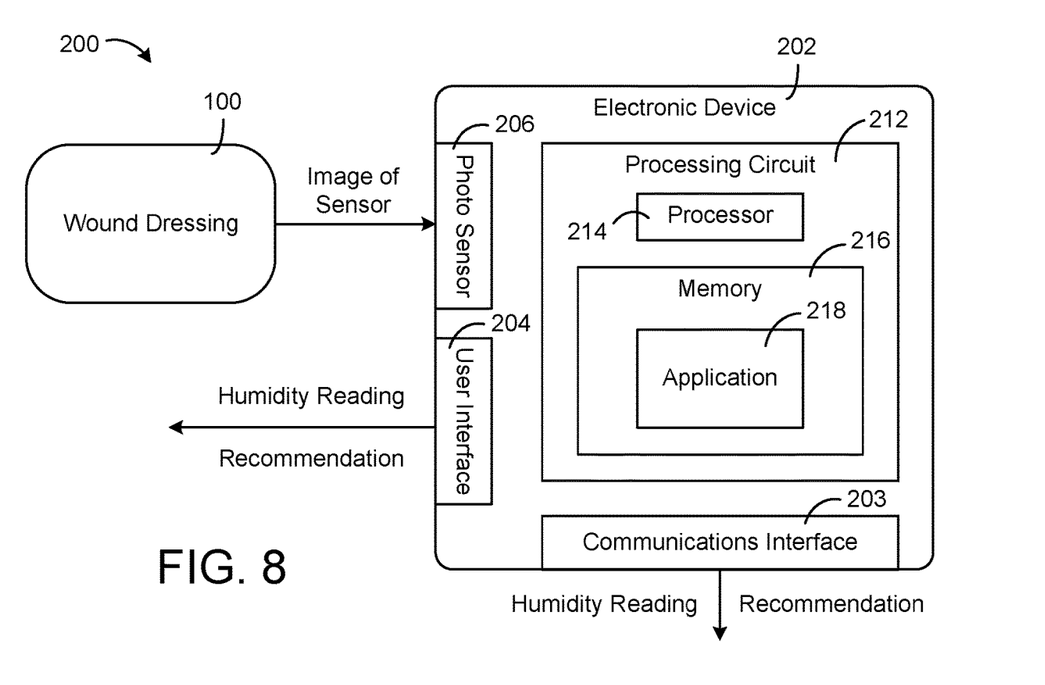
FIG. 8 is a block diagram of the humidity monitoring system of FIG. 7, according to an exemplary embodiment.

Referring now to FIGS. 7-8, a humidity monitoring system 200 is shown, according to an exemplary embodiment. System 200 is shown to include wound dressing 100 and an electronic device 202. In some embodiments, electronic device 202 is a mobile device such as a smartphone, tablet, PDA, laptop computer, or other portable computing device. In some embodiments, electronic device is a therapy device such as a negative pressure wound therapy (NPWT) device or other type of medical device. Electronic device 202 is shown to include a communications interface 203, a processing circuit 212, a photo sensor 206, and a user interface 204.

Communications interface 203 may facilitate communications between electronic device 202 and external systems or devices. Communications interface 203 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 203 can include an Ethernet card and port for sending and receiving data via an Ethernet-based communications link or network. In another example, communications interface 203 can include a Wi-Fi transceiver for communicating via a wireless communications network or cellular or mobile phone communications transceivers.

Processing circuit 212 is shown to include a processor 214 and memory 216. Processor 214 may be a general purpose or specific purpose processor, an application specific integrated circuit (ASIC), one or more field programmable gate arrays (FPGAs), a group of processing components, or other suitable processing components. Processor 214 is configured to execute computer code or instructions stored in memory 216 or received from other computer readable media (e.g., CDROM, network storage, a remote server, etc.).

Memory 216 may include one or more devices (e.g., memory units, memory devices, storage devices, etc.) for storing data and/or computer code for completing and/or facilitating the various processes described in the present disclosure. Memory 216 may include random access memory (RAM), read-only memory (ROM), hard drive storage, temporary storage, non-volatile memory, flash memory, optical memory, or any other suitable memory for storing software objects and/or computer instructions. Memory 216 may include database components, object code components, script components, or any other type of information structure for supporting the various activities and information structures described in the present disclosure. Memory 216 may be communicably connected to processor 214 via processing circuit 212 and may include computer code for executing (e.g., by processor 214) one or more processes described herein. When processor 214 executes instructions stored in memory 216, processor 214 generally configures electronic device 202 (and more particularly processing circuit 212) to complete such activities. In some embodiments, memory 216 stores an application 218 which can be run by processing circuit 212.

As discussed above, humidity colorimeter sensor 102 can be configured to measure the humidity of a wound site and emit or reflect light at a wavelength representative of the humidity of the wound site. In other words, the color of humidity colorimeter sensor 102 may represent the humidity of the wound site. Electronic device 202 can use photo sensor 206 (e.g., a camera) to capture an image 220 of humidity colorimeter sensor 102. In some embodiments, the wavelength of the light emitted or reflected by humidity colorimeter sensor 102 is within a spectrum readable by photo sensor 206. Accordingly, electronic device 202 can determine the humidity of the wound site based on the wavelength of the light.

In some embodiments, electronic device 202 runs an application 218 (e.g., a mobile application) configured to measure or determine the color of humidity colorimeter sensor 102 based on the image 220 captured by photo sensor 206. Application 218 can be any type of application capable of running on electronic device 202 including, for example, the "iOn HEALING" mobile application by Kinetic Concepts, Inc. Application 218 can be configured to determine the humidity of the wound site based on the color of image 220. For example, application 218 may use a lookup table, a function, or other stored relationship to determine a humidity value that corresponds to the measured color. In some embodiments, image 220 is presented to a user via user interface 204. Application 218 can be configured to generate a graphical representation 208 of the humidity value, which can be presented to a user via user interface 204. In some embodiments, the humidity value is communicated to an external system or device via communications interface 203.

In some embodiments, application 218 is configured to generate a recommendation based on the determined humidity value. It may be desirable to achieve a target level of humidity at the wound site to promote effective wound healing. The recommendation generated by application 218 may suggest a user action which will drive the measured humidity level to the target humidity level. For example, the recommendation may include a recommendation to replace wound dressing 100 with a more absorbent wound dressing if the measured humidity level is above the target humidity level (i.e., the wound site is too moist). Conversely, the recommendation may include a recommendation to replace wound dressing 100 with a less absorbent wound dressing if the measured humidity level is below the target humidity level (i.e., the wound site is too dry). The recommendation can be presented to a user via user interface 204 and/or communicated to an external system or device via communications interface 203.

In some embodiments, application 218 is configured to record multiple data points over a period of time. Each data point may include a humidity value and a corresponding timestamp. Application 218 can use the recorded data points to generate and present a time series or graph that indicates the history of humidity values measured over time. In some embodiments, application 218 uses the history of humidity values to determine the rate at which wound exudate is absorbed by wound dressing 100 over time. Application 218 can determine whether the exudate rate is increasing or decreasing. A decreasing exudate rate after one or more dressing changes may indicate that the wound is healing, whereas an increasing or constant exudate rate over time may indicate that the wound is not healing or healing more slowly than expected. By using the history of humidity values to determine whether the wound is healing, application 218 can provide a quantitative confirmation of caregiver intuition. Application 218 can also use rate at which the exudate is increasing or decreasing to determine and recommend an appropriate level of absorbency for the next wound dressing when wound dressing 100 is removed and a new wound dressing is applied.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A wound dressing comprising:
    a superabsorbent pad configured to absorb wound fluid and having a first side and a second, wound-facing side;
    a drape layer coupled to the first side of the superabsorbent pad and having a first side and a second, wound-facing, side, wherein the drape layer is impermeable to liquid and permeable to vapor;
    a humidity chamber coupled to the first side of the drape layer opposite the superabsorbent pad;
    a wick extending through the drape layer and configured to wick moisture between the superabsorbent pad and the humidity chamber; and
    a humidity colorimeter sensor located within the humidity chamber and configured to change color responsive to a humidity level within the humidity chamber.

2. The wound dressing of claim 1, wherein the humidity colorimeter sensor comprises a graphene oxide sensor.

3. The wound dressing of claim 1, wherein the humidity color meter sensor comprises a non-powered humidity sensor.

4. The wound dressing of claim 1, wherein the humidity chamber is impermeable to liquid and permeable to vapor.

5. The wound dressing of claim 1, wherein the humidity chamber is impermeable to both liquid and vapor.

6. The wound dressing of claim 1, wherein the humidity chamber comprises an outer layer having a perimeter adhered to the first side of the drape layer, thereby sealing the humidity colorimeter sensor between the outer layer and the drape layer.

7. The wound dressing of claim 6, wherein:
    the drape layer is configured to transfer moisture vapor through the drape layer at a first moisture vapor transmission rate; and
    the outer layer of the humidity chamber is configured to transfer moisture vapor through the outer layer at a second moisture vapor transmission rate less than the first moisture vapor transmission rate.

8. The wound dressing of claim 1, wherein the humidity chamber comprises:
    an outer layer; and
    an inner layer positioned between the outer layer and the first side of the drape layer and having a perimeter adhered to the outer layer, thereby sealing the humidity colorimeter sensor between the outer layer and the inner layer.

9. The wound dressing of claim 8, wherein the wick extends through both the drape layer and the inner layer of the humidity chamber.

10. The wound dressing of claim 1, wherein the wick comprises:
    a first end portion located between the superabsorbent pad and the drape layer;
    a second end portion located within the humidity chamber; and
    a middle portion extending through the drape layer and connecting the first end portion and the second end portion.

11. The wound dressing of claim 10, wherein:
    the first end portion and the second end portion are parallel to the superabsorbent pad and the drape layer; and
    the middle portion is perpendicular to the superabsorbent pad and the drape layer.

12. The wound dressing of claim 1, wherein the drape layer is configured to wick moisture from the superabsorbent pad and distribute the moisture across the first side of the drape layer.

13. The wound dressing of claim 1, wherein the drape layer extends beyond a perimeter of the superabsorbent pad to provide an adhesive-coated margin configured to adhere the wound dressing to a surface.

14. A wound dressing comprising:
    a superabsorbent pad configured to absorb wound fluid and having a first side and a second, wound-facing side;
    a humidity chamber located on the first side of the superabsorbent pad; and
    a humidity colorimeter sensor located within the humidity chamber and configured to change color responsive to a humidity level within the humidity chamber.

15. The wound dressing of claim 14, further comprising a drape layer positioned between the superabsorbent pad and the humidity chamber, wherein the drape layer is impermeable to liquid and permeable to vapor.

16. The wound dressing of claim 15, further comprising a wick extending through the drape layer and configured to wick moisture between the superabsorbent pad and the humidity chamber.

17. The wound dressing of claim 16, wherein the wick comprises:
    a first end positioned between the superabsorbent pad and the drape layer; a second end positioned within the humidity chamber; and
    a middle portion extending through the drape layer and connecting the first end and the second end.

18. The wound dressing of claim 17, wherein:
the first end portion and the second end portion are parallel to the superabsorbent pad and the drape layer; and
the middle portion is perpendicular to the superabsorbent pad and the drape layer.

19. The wound dressing of claim 15, wherein the humidity chamber comprises an outer layer having a perimeter adhered to the drape layer, thereby sealing the humidity colorimeter sensor between the outer layer and the drape layer.

* * * * *